United States Patent [19]

Collandre et al.

[11] Patent Number: 5,545,520
[45] Date of Patent: Aug. 13, 1996

[54] NUCLEIC ACID FRAGMENTS AND DIAGNOSTIC REAGENTS DERIVED FROM THE HHV6/SIE GENOME AND PROCEDURES FOR DIAGNOSING HHV6 INFECTIONS

[75] Inventors: Helene Collandre, Paris; Luc Montagnier, Le Plessis Robinson; Henri Agut; Jean-Marie Bechet, both of Paris, all of France

[73] Assignees: Institute Pasteur; University Paris - VI, both of Paris, France

[21] Appl. No.: 161,339

[22] Filed: Sep. 7, 1993

Related U.S. Application Data

[63] Continuation of Ser. No. 678,256, filed as PCT/00618, Aug. 17, 1990, abandoned.

[30] Foreign Application Priority Data

Aug. 18, 1989 [FR] France .................................. 89 11016

[51] Int. Cl.$^6$ ...................................................... C12Q 1/70
[52] U.S. Cl. .......................... 435/5; 536/24.32; 536/24.33
[58] Field of Search ........................... 435/5, 91.2, 172.3, 435/235.1; 536/24.32, 24.33, 23.72

[56] References Cited

U.S. PATENT DOCUMENTS 4,683,195  7/1987  Mullis et al. ................................ 435/6

FOREIGN PATENT DOCUMENTS

88/01305  2/1988  WIPO .
88/09814  12/1988  WIPO .

OTHER PUBLICATIONS

Stratagene 1988 Catalog, p. 39.
S. F. Yosephs et al. J. Virological Methods 21, 179–190 (1988).
S. L. Berger and A. R. Kimmel (eds) Methods in Enzymology 152, 91–94, 151–154, 180–199, 713–716 (1987).
Ablashi et al. J. Virological Methods 21, 29–48 (1988).
R. C. Ogden and D. A. Adams Methods in Enzymology 152, 72 (1987).
R. J. Roberts Nucl. Acids Res. 17, r347–r387 (1989).
H. Agut et al. Lancet i, 712 (1988).
Research in Virology, vol. 140, 1989, Elsevier, (Paris, FR), Elsevier, Paris, FR), H. Agut et al.: "Co-cultivation of human Herpervirus 6 and HIV1 from blood lymphocytes", pp. 23–26 voir p. 24, Lignes 8–10; figure 1 (cité dans la demande).
The Lancet, 2/9 janvier 1988, (London, GB), S. Efstathiou et al.: "DNA Homology between a novel human herpesvirus (HHV–6) and human cytomegalovirus", pp. 63–64, voir l'article en entier.
Leukemia, vol. 2, No. 3, mars 1988, Villiams & Wilkins, (Baltimore, US), S. F. Josephs et al.: "Detection of human B–Lymphotropic virus (human herpesvirus 6) sequences in B cell lymphoma tissues of three patients", pp. 132–135, voir p. 132, colonne 2, lignes 45–50; p. 133, colonne 1, lignes 10–12.
Leukemia, vol. 2, No. 8, aout 1988, Williams & Wilkins, (Baltimore, US), R. F. Jarrett et al.: "Identification of human Herpesvirus 6–specific DNA sequences in two patients with non–hodgkin's lymphoma", pp. 496–502 voir p. 498, colonne 1, ligne 15—p. 498, colonne 2, ligne 9.
Journal of Virology, vol. 62, No. 12, Dec. 1988, American Societe for Microbiology, (Washington, DC, US) M. Kishi et al.: "A repeat sequence, GGGTTA, is shared by DNA of human Herpesvirus 6 and Marek's disease virus", pp. 4824–4827 voir p. 4825, figure 2.

*Primary Examiner*—W. Gary Jones
*Assistant Examiner*—Scott W. Houtteman
*Attorney, Agent, or Firm*—Oblon, Spivak, McClelland, Maier & Neustadt, P.C.

[57] ABSTRACT

Nucleic acid fragments derived from the HHV6 virus genome and their use in the diagnosis of infections involving this virus.

9 Claims, 1 Drawing Sheet

NUCLEIC ACID FRAGMENTS AND DIAGNOSTIC REAGENTS DERIVED FROM THE HHV6/SIE GENOME AND PROCEDURES FOR DIAGNOSING HHV6 INFECTIONS

According to another preferred embodiment of the present invention, one of the said double-strand DNA fragments is characterised in that it is obtained by digestion of the genome DNA of the HHV6/SIE virus with the enzyme Bam HI, in that its size is 850 bp and in that it contains the following sequence (SEQ ID No:1)

(I)

```
5' GATCCGACGCCTACAAACACGTCGATAATTTGATATAATAAGTGGAAAACTCTG
TTCCAGAGAAAGGGTGTTGCGAAGGGCTGATTAGGATTAATAGGAGAATCTTGTAAG
TATATGGTCCAGTTGAAATTAGATTTCATTATAGGAAAAGATTTGAGATCGTGAAAT
AAAGATTGAAATTGTGATCGTAGTTCATAAAAACTTGGAATGAGGTCACTTCTGTTG
CGTAATATGTCAAGGATGTCGGTACTTTTTTTCTTTTGACTATTGTCTATGTCTATG
ACATTGAG...-3'
```

This application is a Continuation of application Ser. No. 07/678,256, filed as PCT/FR90/00618, Aug. 17, 1990, now abandoned.

The present invention relates to nucleic acid fragments derived from the HHV6 virus genome, vectors containing the said fragments and their use in the diagnosis of infections involving this virus.

HHV6 viruses, which are viruses containing double strand DNA classified in the Herpes-virus family have been isolated from lymphocytes of patients suffering from AIDS or having lymphoproliferative disorders. These viruses are also regarded as being the causal agent of exanthema subitum.

Various strains of these viruses are known: the HBLV strain, which specifically infects the B lymphocytes, has been described by SALAHUDIN et al. (Science 234, 396, 1986) and in the PCT application WO 88/01387; two other strains have been described by the inventors: the 39 TAN strain (AGUT et al., Res. Virol. 140, 23, 1989) and the SIE strain, which infects the T lymphocytes (AGUT et al., Lancet i, 712, 1988).

The genome of the SIE strain, which is about 160 kb in size, consists of double-strand DNA in essentially linear form; its GC content is between 38 and 40% and it possesses repetitive terminal sequences.

Figure 1:
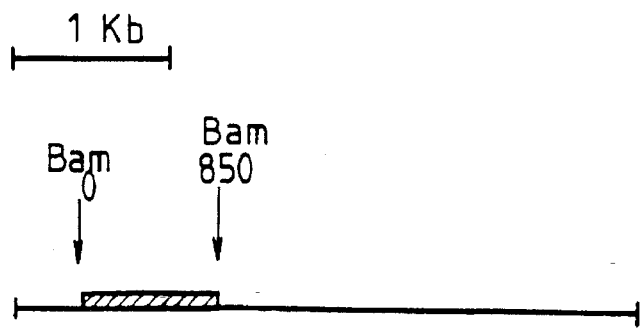
FIG. 1. The restriction map of the plasmid pHC 5.

The aim of the present invention is to provide nucleic acid reagents which permit the diagnosis of HHV6/SIE infections, and also nucleic acid reagents permitting the general diagnosis of infections involving any HHV6 strain. To this end, the inventors have selected, cloned and characterised three fragments of the viral HHV6/SIE genome.

The subject of the present invention is genome DNA fragments of the HHV6/SIE virus, characterised in that they are obtained by digestion by an appropriate restriction enzyme.

According to a preferred embodiment of the present invention, one of the said double-strand DNA fragments is characterised in that it is obtained by digestion of the genome DNA of the HHV6/SIE virus with the enzyme Bam HI, in that its size is 5 kb and in that it contains an EcoRI restriction site 1.8 kb from one of its ends.

This fragment of the HHV6/SIE genome corresponds to a zone of the HHV6 genome which is preserved in all the known strains.

The present invention also encompasses nucleotide sequences which are synthetic, semi-synthetic or obtained by genetic engineering and are derived from DNA fragments as defined above, whether the said sequences are double-strand DNA sequences containing all or part of the sequence of the said fragments, or single-strand DNA or RNA complementary to all or part of one or other strand of the said fragments.

A preferred embodiment of the present invention encompasses, in particular, the following oligonucleotide sequences:

| | |
|---|---|
| 5'-GAXCCGACGCCXACAAACAC-3' | (II) (SEQ ID NOS: 2–3) |
| 5'-XACCGACAXCCXXGACAXAXX AC-3' | (III) (SEQ ID NOS: 4–5) |
| 5'-GGCXGAXXAGGAXXAAXAGGA GA-3' | (IV) (SEQ ID NOS: 6–7) | in which X=T (SEQ ID NOS: 2, 4 and 6) or U (SEQ ID NOS: 3, 5, and 7), and which are derived from sequence (I).

Another preferred embodiment of the present invention comprises nucleotide sequences obtained by the PCR amplification method, using the oligonucleotide sequences (II) and (III), or the oligonucleotide sequences (III) and (IV), as initiators and the HHV6 genome DNA as template, and the respective lengths of which are 249 and 171 bp.

Another preferred embodiment of the present invention comprises recombinant DNA sequences containing all or part of the sequence of one of the HHV6/SIE genome fragments according to the invention, such as, in particular:

the plasmid pHC-147, which results from the insertion of the 5 kb DNA fragment defined above in the plasmid PTZ 19R, and the plasmid pHC-5, which results from the insertion of the 850 bp DNA fragment defined above in the plasmid PTZ 19R.

The subject of the present invention is also transformed eucaryote or procaryote cell clones containing at least one recombinant DNA sequence as defined above.

Clones of the Escherichia coli DH5 strain, transformed by the abovementioned plasmids, are the subject of material filed with the Collection Nationale de Cultures de Microorganismes (CNCM; National Collection of Microorganism Cultures) on 19 Jul. 1989:

the clone transformed by the plasmid pHC-5 bears the file number I-895.

the clone transformed by the plasmid pHC-147 bears the file number I-896.

The subject of the present invention is also diagnostic reagents, characterised in that they contain at least one of the nucleotide sequences derived from the HHV6/SIE virus genome fragments according to the invention, as have been defined above, in combination with at least one appropriate detection means.

The said reagents may be used in a very large number of diagnostic techniques based on the detection of nucleic acids by hybridisation and/or amplification; in particular reagents derived from the 850 bp BamHI fragment, corresponding to a conserved sequence, may permit the detection of all of the HHV6 strains.

The present invention consequently relates to a diagnostic procedure permitting either the detection of the HHV6/SIE virus or, more generally, the detection of the HHV6 virus in a biological sample, characterised in that it comprises a step in which the biological sample is brought into contact with a reagent according to the invention, and a step in which a specific interaction is detected between the said reagent and one or more DNA sequences of the said virus which may be present in the biological sample.

According to a preferred embodiment of this procedure, the detection is carried out by the PCR amplification method (chain amplification by Taq polyrmerase) and oligonucleotide sequences derived from the DNA fragments defined above are used as initiators and, where appropriate, as probes.

According to a preferred version of this embodiment, so as to permit the detection of all of the HHV6 strains, the nucleotide sequences (II) and (III) or the nucleotide sequences (III) and (IV) are used as initiators and the nucleotide sequence (IV) is used, where appropriate, as probe.

The subject of the present invention is also a kit for diagnosing HHV6 and/or HHV6/SIE infections, characterised in that it comprises at least one reagent according to the invention, in combination with means for carrying out a procedure as described above.

The present invention will be better understood with reference to the remainder of the description which follows, which relates to examples of the preparation of the reagents according to the invention and their use for the detection of HHV6.

I—PREPARATION OF NUCLEIC ACID FRAGMENTS AND MOLECULES ACCORDING TO THE INVENTION

A) ISOLATION AND PROPAGATION OF THE HHV6/SIE STRAIN

The HHV6/SIE strain has been isolated from the lymphocytes of a patient suffering from HTLV-1 leukaemia and seropositive for HIV-2.

The virus is propagated on peripheral blood lymphocytes.

The isolation and the propagation of this strain are described in the publication by AGUT et al. (Lancet i, 712, 1988).

B) PRODUCTION AND CHARACTERISATION OF NUCLEIC ACID FRAGMENTS AND MOLECULES ACCORDING TO THE INVENTION

EXAMPLE 1

Production and cloning of 5 kb and 850 bp Bam HI fragments

The DNA extracted from infected BpL (peripheral blood lymphocyte) cells is completely digested by the enzyme Bam HI.

The fragments resulting from the digestion are separated on a 10–30% sucrose gradient.

Fragments having a size smaller than 15 kb are inserted at the Bam HI site of the multifunctional plasmid PTZ 19R and introduced into *E. coli* DH5 bacteria.

The genome library thus obtained is screened using viral DNA isolated from the virion purified on a 10–60% sucrose gradient and labelled with $CTP^{32}P$.

Two recombinants were then selected:

a clone containing the plasmid pHC 5, which comprises a 850 bp insert of HHV6/SIE genome DNA; this clone/was filed on 19 Jul. 1989 with the CNCM under the access number I-895.

FIG. 1 shows the restriction map of the plasmid pHC 5.

The hatched zone indicates the location of the 850 bp insert. This insert does not contain any restriction site for the enzymes Hind III, Kpn I, SacI and SmaI. This insert has been partially sequenced. The sequence corresponding to the first 290 bases is represented by the formula (I).

a clone containing the plasmid pHC 147, which comprises a 5 kb insert of HHV6/SIE genome DNA. This clone was filed on 19 Jul. 1989 with the CNCM under the access number I-896.

Figure 2:
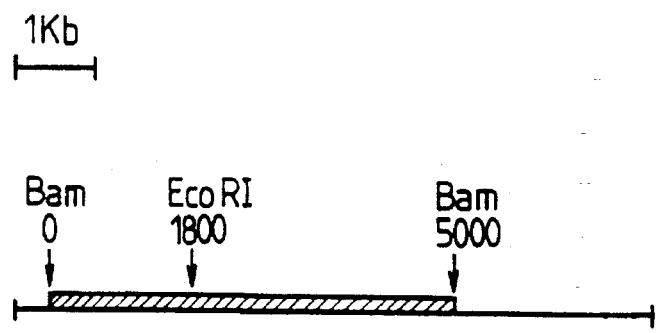
FIG. 2. The restriction map of the plasmid pHC 147.

FIG. 2 shows the restriction map of the plasmid pHC 147.

The hatched zone indicates the location of the 5 kb insert. This insert carries an EcoRI restriction site 1.8 kb from one of its ends. It does not contain any site for the enzymes Sma I, Sal I, Sac I, Kpn I and Xba I.

EXAMPLE 2

Production and cloning of a 3.9 kb Cla I fragment

The procedure is identical to that followed in Example 1 except that the DNA extracted from BpL cells is digested by the enzyme Cla I and that the fragments obtained are inserted at the Cla I site of the plasmid PBR 322.

A recombinant clone was selected from the genome library obtained. This clone contains the plasmid pHC-44, which carries a 3.9 kb insert of the HHV6/SIE genome DNA. It was filed on 19 Jul. 1989 with the CNCM under the access number I-894.

Figure 3:
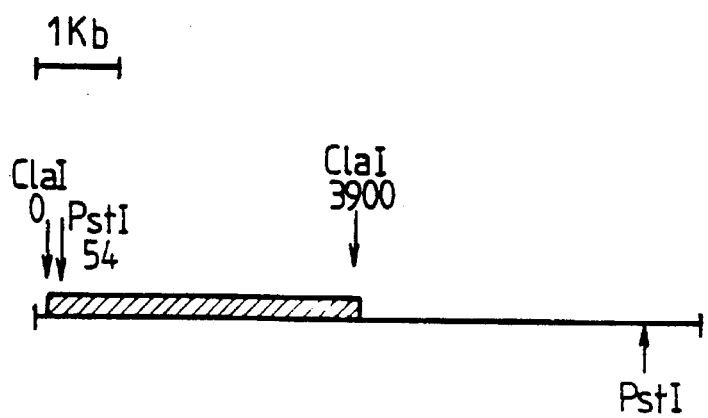
FIG. 3. The restriction map of the plasmid pHC 44.

FIG. 3 shows the restriction map of the plasmid pHC-44.

The hatched zone indicates the location of the 3.9 kb insert. This insert carries a Pst I site 54 bp from one of its ends. It does not contain any Hind III site.

II—DETECTION OF THE PRESENCE OF HHV6 VIRUSES IN A BIOLOGICAL SAMPLE

EXAMPLE 3

Detection procedure using PCR

Synthetic oligonucleotides were obtained from the sequence (I).

the first (A) consists of the sequence (II) which corresponds to the first 20 bases of the sequence (I)

the second (B) consists of the sequence (III), which is complementary to the bases 227 to 249 of the sequence (I).

the third (S) consists of the sequence (IV) and corresponds to the bases 79–101 of the sequence (I).

These oligonucleotides are used in a chain amplification reaction using Taq polymerase.

The reaction mixture contains, for a total volume of 100 µl: 0.1 to 0.5 µM of each of the two initiators (A and B, or B and S), 200 µM of each of the 4 deoxyribonucleotide triphosphates (dATP, dCTP, dGTP, dTTP), 1.5 mM of $MgCl_2$, 50 mM of KCl, 10 mM of Tris-HCl of pH 8.3, 0.1% (wt/vol) of gelatin, one unit of Taq DNA-polymerase (Cetus) and between 0 and 300 ng of the DNA sample likely to contain the sequence to be amplified.

30 amplification cycles are carried out, under the conditions indicated in the following table I:

TABLE I

| STEP | TEMPERATURE | 1ST CYCLE | 2ND/29TH CYCLE | 30TH CYCLE |
|---|---|---|---|---|
| DENATURING | 94° C. | 5 min | 1 min | 1 min |
| HYBRIDISATION | 55° C. | 1 min | 1 min | 1 min |
| POLYMERISATION | 72° C. | 1 min | 1 min | 7 min |

The amplification products are analysed on an agarose gel containing 1 μg/ml of ethidium-bromide and may be detected by measuring the fluorescence at excitation wavelength 254 nm.

The specificity of the amplification reaction is demonstrated by detection of the products of said reaction using the "Southern blotting" technique: the amplification products are transferred from an agarose gel to a nylon membrane (ZETAPROBE); the detection is effected using a $^{32}$P-labelled oligonucleotide S as probe.

When the oligonucleotides A and B are used as initiators, a 249 bp fragment is detected after 30 amplification cycles; when the oligonucleotides B and S are used as initiators, a 171 bp fragment is detected after 30 amplification cycles.

It was possible to detect these two fragments in all of the samples consisting of DNA from cells infected by viruses belonging to the HHV6/HBLV, HHV6/39TAN and HHV6/SIE strains.

The sensitivity of the detection was determined using, as amplification sample, either a plasmid DNA, in which a fragment of the HHV6/SIE virus genome containing the desired sequence has been inserted, or the total DNA of PBL cells infected by HHV6; in the first case, the lower detection limit corresponds to 0.3 fg of DNA; in the second case, it corresponds to 5 fg of DNA.

As follows from the above, the invention is in no way restricted to those of its embodiments, implementations and applications which have Just been described in more detail; on the contrary, it encompasses all of the variants which may be conceived by those skilled in the art, without departing from either the framework or the scope of the present invention.

We claim:

1. Oligonucleotide, characterized in that it consists of the following sequence, in which X=T or U, or its complementary sequence:

5'-GAXCCGACGCCXACAAACAC-3'    SEQ ID NOS: 2–3.

2. Oligonucleotide, characterized in that it consists of the following sequence in which X=T or U, or its complementary sequence:

5'-XACCGACAXCCXXGACAXAXXAC-3'    SEQ ID NOS: 4–5.

3. Oligonucleotide characterized in that it consists of the following sequence in which X=T or U, or its complementary sequence:

5'-GGCXGAXXAGGAXXAAXAGGAGA-3'    SEQ ID NOS: 6–7.

4. Oligonucleotide characterized in that it is obtained by a Polymerase Chain Reaction amplification method, using a first primer having the sequence of SEQ ID NOS: 2–3 and a second primer having the sequence of SEQ ID NOS: 4–5 and the HHV6 genome DNA as a template and in that the length of the oligonucleotide is 249 bp.

5. Detection reagent, containing at least one of the oligonucleotides of claims 1, 2, 3 or 4 in combination with at least one means of detection of hybridization between said oligonucleotide and complementary DNA sequence of HHV6 virus.

6. Procedure for detecting the presence of a HHV6 virus in a biological sample comprising:

contacting the biological sample with a reagent according to claim 5 under hybridization conditions;

hybridizing said sample and reagent;

detecting hybridization between said reagent and complementary DNA sequences of said virus;

wherein the detection of hybridization is indicative of the presence of HHV6 virus.

7. Procedure according to claim 6, comprising a Polymerase Chain Reaction step wherein SEQ ID NOS: 2–3 and SEQ ID NOS: 4–5 or SEQ ID NOS:4–5 and SEQ ID NOS:6–7 are used as primers.

8. Kit for detecting HHV6 or HHV6/SIE infections comprising at least one reagent according to claim 5 in combination with means for carrying out a Polymerase Chain Reaction procedure.

9. Procedure according to claim 7 wherein SEQ ID NOS: 2–3 and SEQ ID NOS: 4–5 or SEQ ID NOS:4–5 and SEQ ID NOS:6–7 are used as primers and SEQ ID NOS:6–7 are used as probes.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 290 base pairs
        ( B ) TYPE: nucleic acid
        ( C ) STRANDEDNESS: unknown
        ( D ) TOPOLOGY: unknown ( i i ) MOLECULE TYPE: DNA (genomic)

( v i ) ORIGINAL SOURCE:
        ( A ) ORGANISM: HHV6/SIE virus ( x i ) SEQUENCE DESCRIPTION: SEQ ID NO:1:

```
GATCCGACGC CTACAAACAC GTCGATAATT TGATATAATA AGTGGAAAAC TCTGTTCCAG      60
AGAAAGGGTG TTGCGAAGGG CTGATTAGGA TTAATAGGAG AATCTTGTAA GTATATGGTC    120
CAGTTGAAAT TAGATTTCAT TATAGGAAAA GATTTGAGAT CGTGAAATAA AGATTGAAAT    180
TGTGATCGTA GTTCATAAAA ACTTGGAATG AGGTCACTTC TGTTGCGTAA TATGTCAAGG    240
ATGTCGGTAC TTTTTTTCTT TTGACTATTG TCTATGTCTA TGACATTGAG              290
```

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA (genomic)

( v i ) ORIGINAL SOURCE:
        ( A ) ORGANISM: HHV6/SIE virus ( x i ) SEQUENCE DESCRIPTION: SEQ ID NO:2:

```
GATCCGACGC CTACAAACAC                                                 20
```

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:3:

GAUCCGACGC CUACAAACAC        20

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: DNA (genomic)

( v i ) ORIGINAL SOURCE:
        ( A ) ORGANISM: HHV6/SIE virus ( x i ) SEQUENCE DESCRIPTION: SEQ ID NO:4:

TACCGACATC CTTGACATAT TAC        23

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:5:

UACCGACAUC CUUGACAUAU UAC        23

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: DNA (genomic)

( v i ) ORIGINAL SOURCE:
        ( A ) ORGANISM: HHV6/SIE virus ( x i ) SEQUENCE DESCRIPTION: SEQ ID NO:6:

GGCTGATTAG GATTAATAGG AGA        23

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:7:

GGCUGAUUAG GAUUAAUAGG AGA        23